US011474114B2

(12) United States Patent
Lee et al.

(10) Patent No.: US 11,474,114 B2
(45) Date of Patent: Oct. 18, 2022

(54) ARTIFICIAL BLOOD FOR BLOODSTAIN PATTERN ANALYSIS

(71) Applicant: REPUBLIC OF KOREA (NATIONAL FORENSIC SERVICE DIRECTOR MINISTRY OF THE INTERIOR AND SAFETY), Wonju-si (KR)

(72) Inventors: Sang Yoon Lee, Wonju-si (KR); Young Il Seo, Wonju-si (KR); Dong A Lim, Daejeon (KR); Kyung Mi Kim, Namyangju-si (KR); Eun Ah Joo, Yongin-si (KR); Je Hyun Lee, Wonju-si (KR); Ki Hwan Kim, Busan (KR); Jin Pyo Kim, Daejeon (KR); Jae Mo Goh, Wonju-si (KR); Nam Kyu Park, Bucheon-si (KR); Se Hyun Shin, Seoul (KR)

(73) Assignee: REPUBLIC OF KOREA (NATIONAL FORENSIC SERVICE DIRECTOR MINISTRY OF THE INTERIOR AND SAFETY), Wonju-si (KR)

( * ) Notice: Subject to any disclaimer, the term of this patent is extended or adjusted under 35 U.S.C. 154(b) by 77 days.

(21) Appl. No.: 17/077,399

(22) Filed: Oct. 22, 2020

(65) Prior Publication Data

US 2021/0396770 A1    Dec. 23, 2021

(30) Foreign Application Priority Data

Jun. 19, 2020    (KR) .................... 10-2020-0075161

(51) Int. Cl.
*G01N 33/72* (2006.01)
*G01N 33/80* (2006.01)
(Continued)

(52) U.S. Cl.
CPC .......... *G01N 33/721* (2013.01); *G01N 33/80* (2013.01); *G01N 33/49* (2013.01); *G01N 33/96* (2013.01);
(Continued)

(58) Field of Classification Search
CPC ...... G01N 33/48; G01N 33/49; G01N 33/721; G01N 33/80; G01N 33/68; G01N 33/96;
(Continued)

(56) References Cited

U.S. PATENT DOCUMENTS 3,852,415 A * 12/1974 Vandervoorde ........ G01N 33/96
250/303
3,911,138 A * 10/1975 Clark, Jr. ............. A61K 31/025
436/15
10,485,756 B2 * 11/2019 Eckelt .................... A61K 47/02

FOREIGN PATENT DOCUMENTS

KR    10-1970300 B1    4/2019

OTHER PUBLICATIONS

Lee et al. Forensic Science International, vol. 316, pp. 1-12, Aug. 19, 2020.*
(Continued)

*Primary Examiner* — Maureen Wallenhorst
(74) *Attorney, Agent, or Firm* — Hauptman Ham, LLP

(57) ABSTRACT

Artificial blood for a bloodstain pattern analysis includes water, an amino acid solution, bovine serum albumin, hemoglobin from bovine blood, potassium ferricyanide, sodium hyaluronate, sodium chloride, and tar color.

7 Claims, 12 Drawing Sheets
(6 of 12 Drawing Sheet(s) Filed in Color)

(51) Int. Cl.
　　　*G01N 33/49*　　　(2006.01)
　　　*G01N 33/96*　　　(2006.01)

(52) U.S. Cl.
　　　CPC .... *Y10T 436/10* (2015.01); *Y10T 436/106664* (2015.01)

(58) Field of Classification Search
　　　CPC ......... Y10T 436/10; Y10T 436/105831; Y10T 436/106664; Y10T 436/108331
　　　USPC ................. 436/8, 15, 16, 18, 66, 84, 86, 88; 252/408.1
　　　See application file for complete search history.

(56) References Cited

OTHER PUBLICATIONS

[Supportive Materials for Exception to Loss of Novelty] Sang-Yoon Lee, "The development of forensic Arlilicial blood substitute: Focusing on Bloodstain pattern analysis", International Association of Bloodstain Pattern Analysts (IABPA) 2019 Annual Conference, Oct. 29, 2019-Nov. 1, 2019, Chicago, USA.

\* cited by examiner

| SURFACE | ITEM | | | | |
|---|---|---|---|---|---|
| | HUMAN BLOOD | EXAMPLE 1 OR 2 | COMPARATIVE EXAMPLE 1 (COMPANY A) | COMPARATIVE EXAMPLE 2 (COMPANY S) | COMPARATIVE EXAMPLE 3 (COMPANY T) |
| 1 A4 PAPER (POROUS SURFACE) | | | | | |
| 2 GLASS PLATE (NON-POROUS SURFACE) | | | | | |
| 3 STAINLESS PLATE (NON-POROUS SURFACE) | | | | | |

ARTIFICIAL BLOOD FOR BLOODSTAIN PATTERN ANALYSIS

CROSS-REFERENCE TO RELATED APPLICATION

This application claims the benefit of Korean Patent Application No. 10-2020-0075161, filed on Jun. 19, 2020, in the Korean Intellectual Property Office, the disclosure of which is incorporated herein in its entirety by reference.

BACKGROUND

1. Field

One or more embodiments relate to artificial blood for a bloodstain pattern analysis.

2. Description of the Related Art

A suspect may be estimated and the authenticity of a suspect's statement may be determined through an analysis of the shape of various bloodstains observed at the scene of the bloodshed. Through a bloodstain pattern analysis, it is possible to reconstruct the crime scene by grasping actions between the perpetrator and the victim. As such, the bloodstain pattern analysis plays an important role in solving crime cases.

Therefore, education and experiments for the bloodstain pattern analysis are necessary to properly solve a bloodshed event. When blood is required for the education and experiments for the bloodstain pattern analysis, human blood obtained through blood collection of a subject, animal (pork or cow) blood supplied from a slaughterer, or artificial blood currently on the market is used.

In the case of human blood, there are problems such as subject's rejection of blood collection, a possibility of odor and decay, a risk of biological infection, a problem of supplying a large amount of blood, and difficulty in controlling experimental conditions according to changes in physical properties due to the use of anticoagulants.

In the case of animal blood, there are problems such as a possibility of odor and decay, a risk of biological infection, difficulty in supply and demand due to low marketability, and difficulty in controlling experimental conditions due to differences in physical properties with human blood.

In the case of artificial blood that is currently manufactured and sold, there are problems such as economic burden due to high price and lack of verification through a comparative experiment of similarity in physical properties with human blood. In addition, because the artificial blood currently manufactured and sold is separately manufactured and sold as shape reproducing artificial blood (spatter blood) and experimental artificial blood (synthetic blood) with a Luminol reaction function, so there is an inconvenience of separately purchasing according to the purpose of the experiment.

[Prior art document] Korean Patent No. 10-1970300 (registered on Apr. 12, 2019)

SUMMARY

One or more embodiments include artificial blood for a bloodstain pattern analysis that may be effectively used for bloodstain pattern analysis education and experiment by adding functional properties such as luminol reaction force and staining power of bloodstains with metamorphosis while realizing properties closer to those of human blood.

One or more embodiments include artificial blood for a bloodstain pattern analysis that may contribute to the analysis and resolution of crime cases because the artificial blood excludes ingredients harmful to the human body as much as possible and is similar to human blood.

According to one or more embodiments, artificial blood for the bloodstain pattern analysis includes water, an amino acid solution, bovine serum albumin, hemoglobin from bovine blood, potassium ferricyanide, sodium hyaluronate, sodium chloride, and tar color.

The amino acid solution may include L-serine, glycine, DL-alanine, L-lysine, L-leucine, L-threonine, L-asparagin anhydrous, L-histidine, L-valine, sodium chloride, magnesium chloride hexahydrate, calcium chloride anhydrous, and zinc chloride.

The artificial blood for the bloodstain pattern analysis may include 25% to 30% by weight of water, 40% to 50% by weight of amino acid solution, 0.5% to 2% by weight of bovine serum albumin, 0.01% to 0.2% by weight of hemoglobin from bovine blood, 1.5% to 3% by weight of potassium ferricyanide, and 20% to 25% by weight of sodium hyaluronate, 0.5% to 1.5% by weight of sodium chloride, and 0.6% to 2% by weight of tar color with respect to 100% by weight of the artificial blood for the bloodstain pattern analysis.

The artificial blood for the bloodstain pattern analysis may include 4.5% to 5.5% by weight of L-serine, 2.5% to 3.5% by weight of glycine, 1.0% to 2.0% by weight of DL-alanine, 1.5% to 2.5% by weight of L-lysine, 0.1% to 1.0% by weight of L-leucine, 0.5% to 1.0% by weight of L-threonine, 0.5% to 1.0% by weight of L-anhydrous asparagine, 0.5% to 1.0% by weight of L-histidine, 0.1% to 0.8% by weight of L-valine, 30% to 40% by weight of sodium chloride, 0.0001% to 0.0005% by weight of magnesium chloride hexahydrate, 0.0001% to 0.0015% by weight of calcium chloride anhydrous, and 0.0001% to 0.0005% by weight of zinc chloride with respect to 100% by weight of the artificial blood for the bloodstain pattern analysis.

The artificial blood for the bloodstain pattern analysis may further include phenoxyethanol acting as a preservative.

The artificial blood for the bloodstain pattern analysis may include 0.1% to 0.7% by weight of phenoxyethanol with respect to 100% by weight of the artificial blood for the blood pattern analysis.

In this case, the tar color may include food tar color Red No. 504 (R #504) and food tar color Violet No. 401 (V #401).

Additional aspects will be set forth in part in the description which follows and, in part, will be apparent from the description, or may be learned by practice of the presented embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the embodiments, taken in conjunction with the accompanying drawings in which.

DETAILED DESCRIPTION

Figure 1:
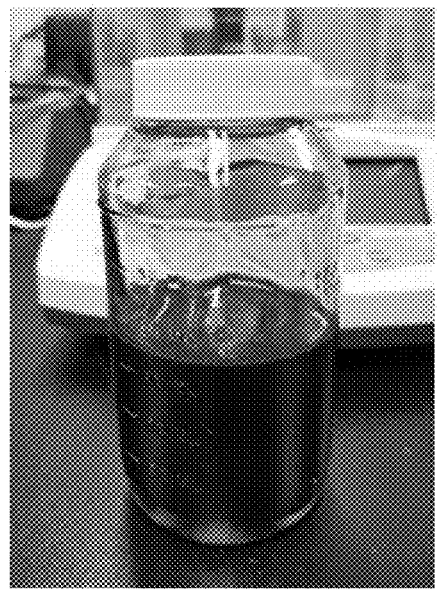
FIG. 1 is a view of artificial blood for a bloodstain pattern analysis according to Example 1 or 2 of the disclosure.

It should be noted that in the following description, only parts necessary for understanding embodiments of the disclosure will be described, and descriptions of other parts will be omitted without departing from the scope of the disclosure.

The terms or words used in the present specification and claims described below should not be construed as being limited to ordinary or lexical meanings, and should be interpreted as meaning and concept corresponding to the technical idea of the disclosure based on the principle that the inventor may appropriately define the concept of a term in order to explain his or her invention in the best way. Therefore, because the configurations shown in the embodiments and drawings described in this specification are merely preferred embodiments of the disclosure and do not represent all of the technical idea of the disclosure, it should be understood that there may be various equivalents and modifications that can replace them at the time of this application.

Hereinafter, embodiments will be described in more detail with reference to the accompanying drawings.

According to one or more embodiments, artificial blood for a bloodstain pattern analysis includes water, an amino acid solution, bovine serum albumin, hemoglobin from bovine blood, potassium ferricyanide, sodium hyaluronate, sodium chloride, and tar color.

The amino acid solution according to an embodiment may include L-serine, glycine, DL-alanine, L-lysine, L-leucine, L-threonine, L-asparagin anhydrous, L-histidine, L-valine, sodium chloride, magnesium chloride hexahydrate, calcium chloride anhydrous, and zinc chloride.

At this time, the higher the content ratio of water and amino acid solution in the artificial blood for the bloodstain pattern analysis according to an embodiment, the higher the surface tension.

The amino acid solution and bovine serum albumin may be stained in response to protein staining reagents, allowing staining of bloodstains with metamorphosis (bloody fingerprints, bloody footprints, etc.).

Hemoglobin from bovine blood and potassium ferricyanide contain iron components, and may exhibit luminescence in response to luminol.

The sodium hyaluronate makes it possible to implement viscosity and viscoelastic properties of the artificial blood for the bloodstain pattern analysis according to an embodiment.

The sodium chloride makes it possible to implement osmotic properties of human blood in the artificial blood for the bloodstain pattern analysis according to an embodiment.

Meanwhile, the tar color allows the artificial blood for the bloodstain pattern analysis according to an embodiment to implement a color similar to that of human blood.

With respect to 100% by weight of the artificial blood for the bloodstain pattern analysis according to an embodiment, 25% to 30% by weight of water, 40% to 50% by weight of amino acid solution, 0.5% to 2% by weight of bovine serum albumin, 0.01% to 0.2% by weight of hemoglobin from bovine blood, 1.5% to 3% by weight of potassium ferricyanide, 20% to 25% by weight of sodium hyaluronate, 0.5% to 1.5% by weight of sodium chloride, and 0.6% to 2% by weight of tar color may be included.

The content ratio of water and the amino acid in the artificial blood for the bloodstain pattern analysis according to an embodiment may be about 1.5 to 2 times greater than the content ratio of water and amino acid in human blood.

With respect to 100% by weight of the artificial blood for the bloodstain pattern analysis according to an embodiment, 4.5% to 5.5% by weight of L-serine, 2.5% to 3.5% by weight of glycine, 1.0% to 2.0% by weight of DL-alanine, 1.5% to 2.5% by weight of L-lysine, 0.1% to 1.0% by weight of L-leucine, 0.5% to 1.0% by weight of L-threonine, 0.5% to 1.0% by weight of L-anhydrous asparagine, 0.5% to 1.0% by weight of L-histidine, 0.1% to 0.8% by weight of L-valine, 30% to 40% by weight of sodium chloride, 0.0001% to 0.0005% by weight of magnesium chloride hexahydrate, 0.0001% to 0.0015% by weight of calcium chloride anhydrous, and 0.0001% to 0.0005% by weight of zinc chloride may be included.

The tar color may include food tar color Red No. 504 (R #504) and food tar color Violet No. 401 (V #401).

With respect to 100% by weight of the artificial blood for the bloodstain pattern analysis according to an embodiment, the food tar color R #504 may be 0.5% to 1.5% by weight and the food tar color V #401 may be 0.1% to 0.5% by weight. Food tar color is used as a colorant and is synthesized from benzene or naphthalene contained in coal tar, but it has low toxicity and water solubility for safety reasons.

The artificial blood for the bloodstain pattern analysis according to an embodiment may implement physical properties similar to those of human blood in consideration of properties such as viscosity, surface tension, and viscoelasticity. In addition, it is preferable to use material components that are not harmful to the human body in the artificial blood for the bloodstain pattern analysis according to an embodiment.

According to another embodiment, the artificial blood for the bloodstain pattern analysis may further include a phenoxyethanol acting as a preservative.

At this time, with respect to 100% by weight of artificial blood for a bloodstain pattern analysis, 0.1 to 0.7% by weight of phenoxyethanol may be included. As such, according to an embodiment, phenoxyethanol, a preservative that does not interfere with the realization of physical properties of the artificial blood for the bloodstain pattern analysis, may be further mixed to prolong storage.

Hereinafter, the disclosure will be described in more detail by describing Examples, Comparative Examples, and Experimental Examples. However, the Examples, Comparative Examples, and Experimental Examples are only examples of the disclosure, and the scope of the disclosure is not limited thereto.

Example 1 and Example 2 are prepared with the composition shown in Table 1, respectively. FIG. 1 shows artificial blood for a bloodstain pattern analysis according to Example 1 or 2 of the disclosure.

Example 1

Example 1 contains, with respect to 100 g % of artificial blood for a bloodstain pattern analysis, 27.40 g % of water, 45.00 g % of amino acid solution, 1.00 g % of bovine serum albumin, 0.15 g % of hemoglobin from bovine blood, 2.30 g % of potassium ferricyanide, 22.00 g % of sodium hyaluronate, 0.90 g % of sodium chloride, 1.00 g % of food tar color R #504, and 0.25 g % of food tar color V #401.

Here, the amino acid solution contains, with respect to 100 g % of the artificial blood for the bloodstain pattern analysis, 5.1654 g % of L-serine, 3.0992 g % of glycine, 1.5496 g % of DL-alanine, 2.0556 g % of L-lysine, 0.5165 g % of L-leucine, 0.7695 g % of L-threonine, 0.7695 g % of L-anhydrous asparagine, 0.7695 g % of L-histidine, 0.5165 g % of L-Valine, 34.7873 g % of sodium chloride, 0.0002 g % of magnesium chloride hexahydrate, 0.0008 g % of anhydrous calcium chloride, and 0.0001 g % of zinc chloride.

Example 2

Example 2 adds phenoxyethanol to the composition of Example 1. At this time, water is 27.00 g %, phenoxyethanol is 0.40 g %.

TABLE 1

Experimental Formula Sheet

| No. | Material | | Artificial Blood Content (g, %) | | |
|---|---|---|---|---|---|
| | | | Type-1 (Not Preservative) | | Type-2 |
| 1 | Water | | | 27.40 | 27.00 |
| 2 | Amino Acid Solution | L-Serine | 45.00 | 5.1654 | 45.00 5.1654 |
| | | Glycine | | 3.0992 | 3.0992 |
| | | DL-Alanine | | 1.5496 | 1.5496 |
| | | L-Lysine | | 2.0556 | 2.0556 |
| | | L-Leucine | | 0.5165 | 0.5165 |
| | | L-Threonine | | 0.7695 | 0.7695 |
| | | L-Asparagin Anhydrous (Asparagin acid) | | 0.7695 | 0.7695 |
| | | L-Histidine | | 0.7695 | 0.7695 |
| | | L-Valine | | 0.5165 | 0.5165 |
| | | Sodium chloride | | 34.7873 | 34.7873 |
| | | Magnesium chloride hexahydrate | | 0.0002 | 0.0002 |
| | | Calcium chloride anhydrous | | 0.0008 | 0.0008 |
| | | Zinc chloride | | 0.0001 | 0.0001 |
| 3 | Bovine Serum Albumin | | | 1.00 | 1.00 |
| 4 | Hemoglobin From Bovine Blood | | | 0.15 | 0.15 |
| 5 | Potassium Ferricyanide | | | 2.30 | 2.30 |
| 6 | Sodium Hyaluronate | | | 22.00 | 22.00 |
| 7 | Sodium Chloride | | | 0.90 | 0.90 |
| 8 | food tar color (R# 504) | | | 1.00 | 1.00 |
| 9 | food tar color (V# 401) | | | 0.25 | 0.25 |
| 10 | Phenoxyethanol | | | | 0.40 |
| | Total | | | 100.00 | 100.00 |

Comparative Examples 1 to 6

Comparative Example 1 is Spatter blood of American Company A, Comparative Example 2 is Spatter blood of American Company S, and Comparative Example 3 is Spatter blood of American Company T. In addition, Comparative Example 4 is Synthetic blood of American company A, Comparative Example 5 is Synthetic blood of American company S, and Comparative Example 6 is Synthetic blood of American company T.

The artificial bloods of Example 1 or 2 and Comparative Examples 1 to 6 are evaluated by methods of Experimental Examples 1 to 6 below.

Experimental Example 1: Comparison of Physical Properties

By comparing physical properties of viscosity, surface tension, and viscoelasticity of human blood, Example 1 or 2, and Comparative Examples 1 to 3, the similarity between Example 1 or 2 and Comparative Examples 1 to 3 and the human blood may be confirmed.

A viscometer (DV-III ULTRA, BROOKFIELD, USA), a surface tension meter (K11, KRUSS, Germany), a viscoelasticity meter (ARES-G2, TA, Germany) are used for measurement comparison. For human blood, Example 1 or 2, and Comparative Examples 1 to 3, under the same temperature (37° C.), the physical properties of viscosity, surface tension, and viscoelasticity are measured 150 times, 10 times each with the same equipment settings.

Experimental Example 1-1: Comparison of Viscosity Properties

TABLE 2

Measured Data Table [Viscosity]

| No. | Item | Temperature [° C.] | Viscosity Detection Speed [RPM] | Viscosity [mPa·s, CP] |
|---|---|---|---|---|
| 1 | Human blood | 37 | 30 | 4.2 |
| 2 | Comparative Example 1 (Company A) | | | 0.7 |
| 3 | Comparative Example 2 (Company S) | | | 0.9 |
| 4 | Comparative Example 3 (Company T) | | | 0.9 |
| 5 | Example 1 or 2 | | | 4.3 |

Figure 2:
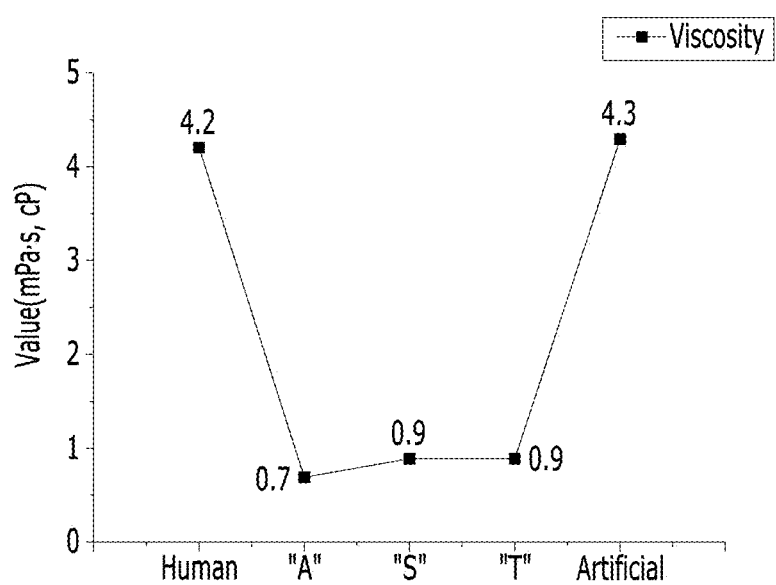
FIG. 2 is a graph comparing viscosity properties of human blood, Example 1 or 2, and Comparative Examples 1 to 3.

FIG. 2 is a graph comparing viscosity properties of human blood, Example 1 or 2, and Comparative Examples 1 to 3. In Table 2 and FIG. 2, the viscosity of human blood is 4.3 [mPa·s, cP], the viscosity of Example 1 or 2 is 4.2 [mPa·s, cP], which is the closest to that of human blood, and the viscosity of Comparative Examples 1 to 3 is 1.0 [mPa·s, cP] or less, which is different from the viscosity of human blood.

Experimental Example 1-2: Comparison of Surface Tension Properties

TABLE 3

Measured Data Table [Surface Tension]

| No. | Item | Temperature [° C.] | Surface Detection Speed [mm/min] | Surface Tension [mN/m] |
|---|---|---|---|---|
| 1 | Human blood | 37 | 10 | 46.58 |
| 2 | Comparative Example 1 (Company A) | | | 38.93 |
| 3 | Comparative Example 2 (Company S) | | | 45.41 |
| 4 | Comparative Example 3 (Company T) | | | 43.46 |
| 5 | Example 1 or 2 | | | 46.80 |

Figure 3:
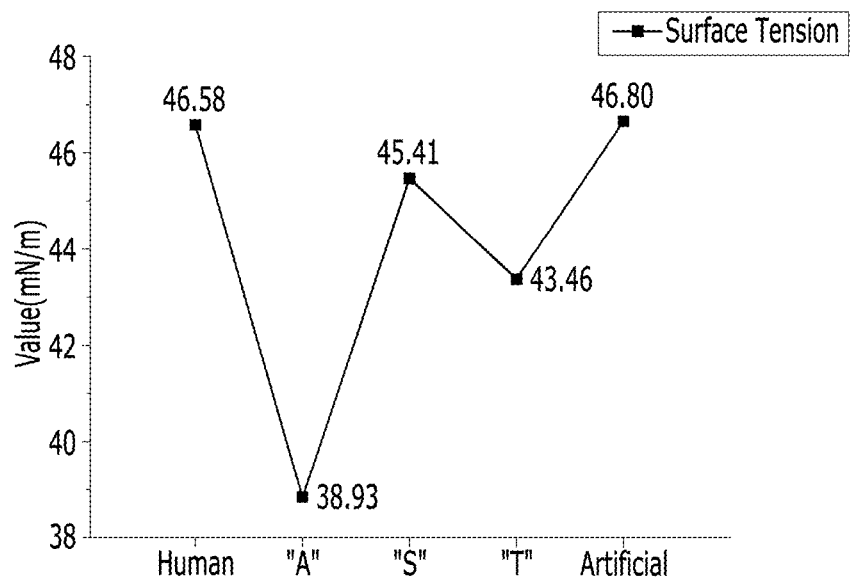
FIG. 3 is a graph comparing surface tension properties of human blood, Example 1 or 2, and Comparative Examples 1 to 3.

FIG. 3 is a graph comparing surface tension properties of human blood, Example 1 or 2, and Comparative Examples 1 to 3. In Table 3 and FIG. 3, the surface tension of human blood is 46.58 mN/m, and the surface tension of Example 1 or 2 is 46.80 mN/m, which is the closest to the surface tension of human blood.

Experimental Example 1-3: Comparison of Viscoelastic Properties

TABLE 4

Measured Data Table [Viscoelasticity]

| No. | Item | Temperature [° C.] | Frequency [Hz] | Viscoelasticity [Pa·s] |
|---|---|---|---|---|
| 1 | Human blood | 37 | 1 | 0.135 |
| 2 | Comparative Example 1 (Company A) | | | 0.008 |
| 3 | Comparative Example 2 (Company S) | | | 0.013 |
| 4 | Comparative Example 3 (Company T) | | | 0.012 |
| 5 | Example 1 or 2 | | | 0.148 |

Figure 4:
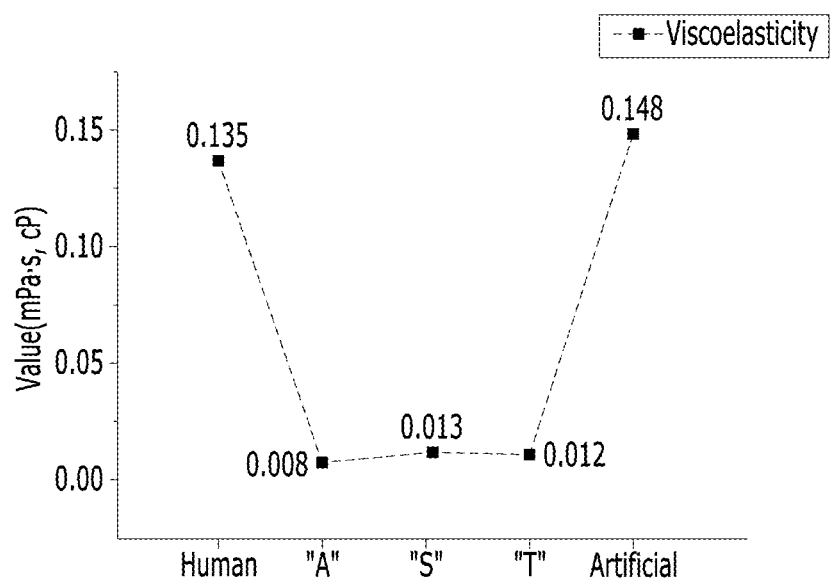
FIG. 4 is a graph comparing viscoelastic properties of human blood, Example 1 or 2, and Comparative Examples 1 to 3.

FIG. 4 is a graph comparing viscoelastic properties of human blood, Example 1 or 2, and Comparative Examples 1 to 3. In Table 4 and FIG. 4, the viscoelasticity of human blood is 0.135 Pa·s, the viscoelasticity of Example 1 or 2 is 0.148 Pa·s, which is the closest to that of human blood, and the viscoelasticity of Comparative Examples 1 to 3 is different from the viscoelasticity of human blood.

As such, it can be seen that Example 1 or 2 shows a value closer to that of human blood in comparison results of all physical properties of viscosity, surface tension, and viscoelasticity than Comparative Examples 1 to 3.

Experimental Example 2: Comparison of Falling Bloodstain Pattern Properties

By comparing characteristics of falling bloodstain patterns for each surface, such as porous and non-porous surfaces of human blood, Example 1 or 2, and Comparative Examples 1 to 3, the similarity between Example 1 or 2 and Comparative Examples 1 to 3 and the human blood may be confirmed.

In this comparative experiment, A4 paper (a porous surface), a glass plate (a non-porous surface), and a stainless plate (a non-porous surface) are used for discrimination power for each surface.

For human blood, Example 1 or 2, and Comparative Examples 1 to 3, falling bloodstains are generated on each surface under the same conditions of temperature of 37° C., capacity of 20 µl, height of 30 cm, and angle of 90° (angle of 90° between each surface and each falling bloodstain).

Figures 5, 6:
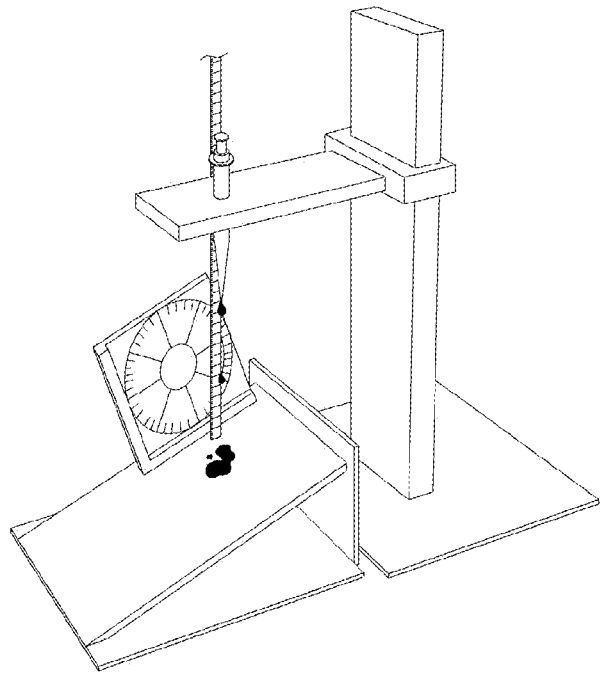
FIG. 5 is a view comparing the characteristics of falling bloodstain patterns for each surface of human blood, Example 1 or 2, and Comparative Examples 1 to 3.
FIG. 6 is a view of a falling bloodstain generator used in an experiment of the disclosure.

FIG. 5 is a view comparing the characteristics of falling bloodstain patterns for each surface of human blood, Example 1 or 2, and Comparative Examples 1 to 3.

As a result of the comparative experiment shown in FIG. 5, in the A4 paper (porous surface), each blood similarly exhibits characteristics of a circular falling bloodstain pattern of 1 mm or less. On the other hand, in the glass plate (non-porous surface) and the stainless plate (non-porous surface), human blood and Example 1 or 2 similarly exhibit characteristics of a circular falling bloodstain pattern that is close to 1 mm to 1.5 mm in circular shape but more widely spread.

As such, it can be seen that Example 1 or 2 exhibits characteristics of falling bloodstain patterns more similar to those of human blood compared to Comparative Examples 1 to 3.

Experimental Example 3: Comparison of Coordinate Characteristics of Impact Angles of Falling Bloodstains By comparing coordinate characteristics of impact angles of falling bloodstains between human blood, Example 1 or 2, and Comparative Examples 1 to 3, the similarity between Example 1 or 2 and Comparative Examples 1 to 3 and human blood may be confirmed.

FIG. 6 is a view of a falling bloodstain generator used in an experiment of the disclosure. In this comparative experiment, each blood is tested a total of 1000 times, 40 times for each angle, under the same conditions of temperature of 37° C., capacity of 20 μl, height of 30 cm, angles of 20°, 30°, 40°, 50°, 60°, and 70° using the falling bloodstain generator of FIG. 6. Derived experimental values are analyzed using Hemospat (Queen's Univ., Canada) and NST (National Forensic Service, Korea) software.

Figure 7:
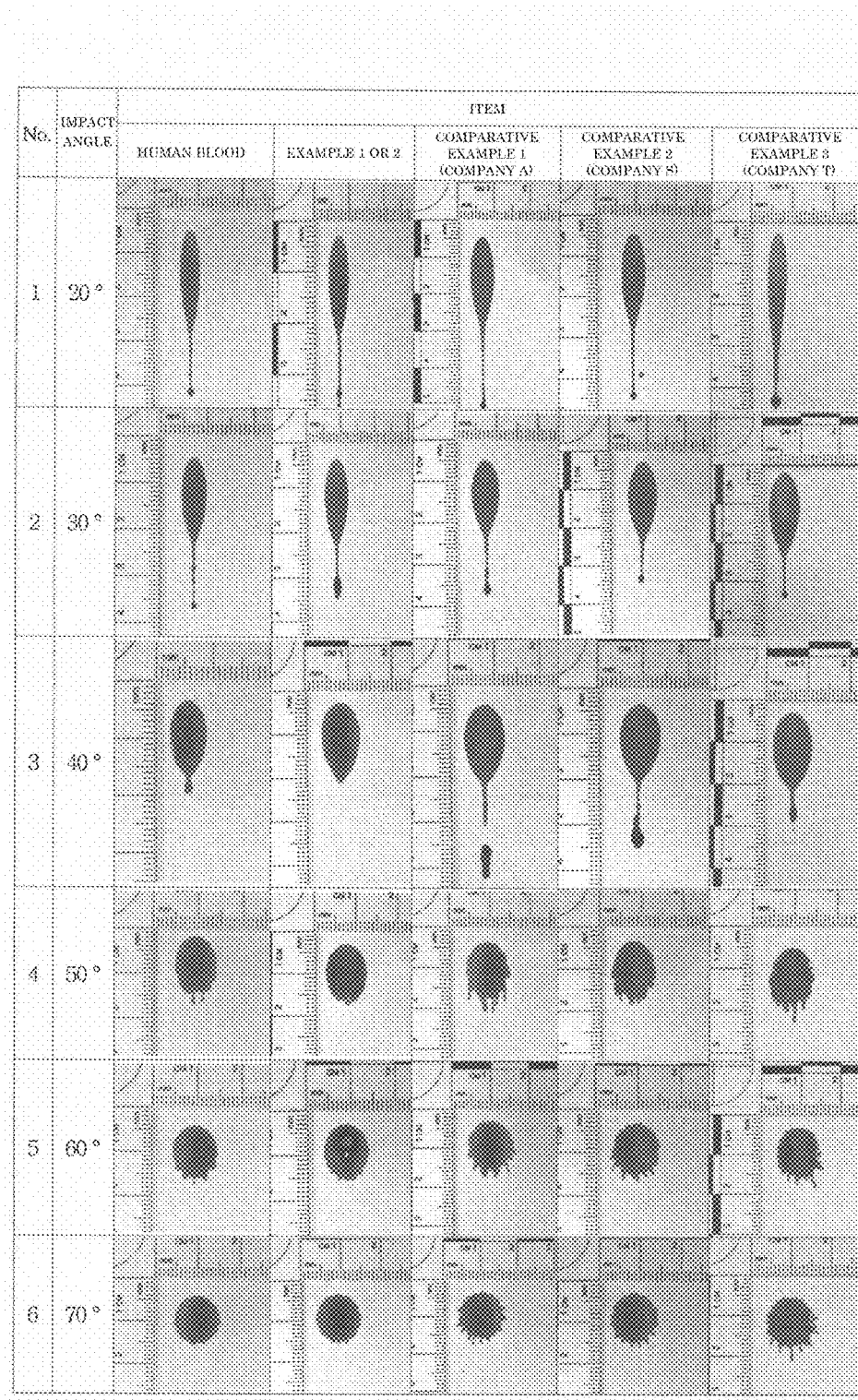
FIG. 7 is a view comparing the characteristics of falling bloodstain patterns for each angle of human blood, Example 1 or 2, and Comparative Examples 1 to 3.

FIG. 7 is a view comparing the characteristics of falling bloodstain patterns for each angle of human blood, Example 1 or 2, and Comparative Examples 1 to 3.

Table 5 shows result data of coordinate characteristics of impact angles of falling bloodstains according to the angles of human blood, Example 1 or 2, and Comparative Examples 1 to 3. At this time, the result data of coordinate characteristics of impact angles of falling bloodstains shows an average value of impact angles (angles in Table 5) of the falling bloodstains by measuring an average value of width (W)/length (L) of the falling bloodstains for a change in actual angles formed by a surface where falling bloodstains are formed and each falling bloodstain. The impact angle is a value represented by arc sin (W/L).

TABLE 5

| | Item | McDonnell formula | Actual angle | | | | | |
|---|---|---|---|---|---|---|---|---|
| | | | 20° | 30° | 40° | 50° | 60° | 70° |
| 1 | Human blood | W/L (ave.) | 0.32 | 0.48 | 0.63 | 0.74 | 0.86 | 0.93 |
| | | angle (ave.) | 18.8 | 28.8 | 39.0 | 48.2 | 58.8 | 68.9 |
| 2 | Comparative Example 1 (Company A) | W/L (ave.) | 0.29 | 0.42 | 0.56 | 0.75 | 0.87 | 0.95 |
| | | angle (ave.) | 14.9 | 24.9 | 34.4 | 48.4 | 61.3 | 71.3 |
| 3 | Comparative Example 2 (Company S) | W/L (ave.) | 0.26 | 0.43 | 0.57 | 0.76 | 0.87 | 0.92 |
| | | angle (ave.) | 15.1 | 25.8 | 34.5 | 49.3 | 60.6 | 69.4 |
| 4 | Comparative Example 3 (Company T) | W/L (ave.) | 0.26 | 0.4 | 0.59 | 0.72 | 0.85 | 0.93 |
| | | angle (ave.) | 14.2 | 23.6 | 36.1 | 46.2 | 58.8 | 69 |
| 5 | Example 1 or 2 | W/L (ave.) | 0.31 | 0.48 | 0.62 | 0.75 | 0.86 | 0.93 |
| | | angle (ave.) | 18.0 | 28.0 | 39.0 | 48.9 | 58.8 | 68.1 |

As a result of the comparative experiments shown in FIG. 7 and Table 5, Example 1 or 2 and Comparative Examples 1 to 3 show results closer to those of human blood at 50°, 60°, and 70°. At smaller angles of 20°, 30°, and 40°, Example 1 or 2 shows result values closer to those of human blood than Comparative Examples 1 to 3.

Figure 8:
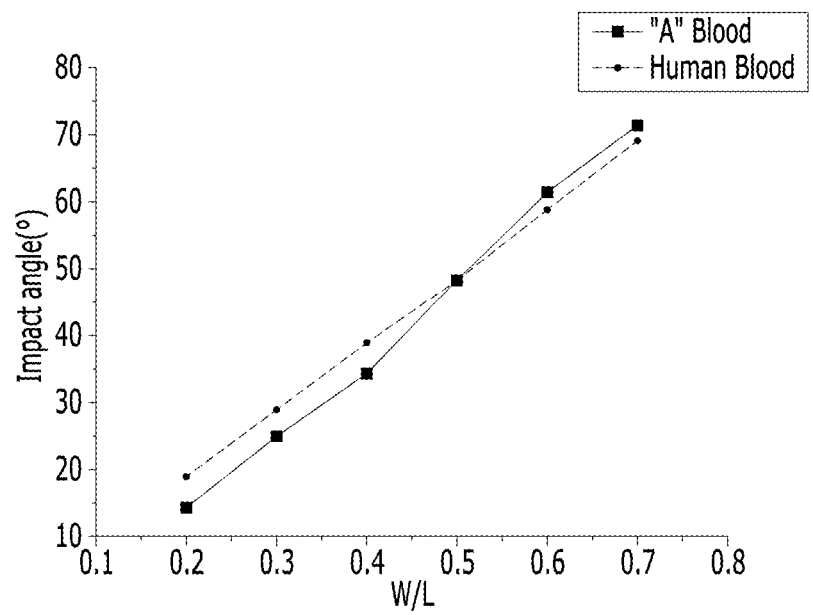
FIG. 8 is a graph showing the comparison of coordinate characteristics of impact angles of falling bloodstains between human blood and Comparative Example 1.
Figure 9:
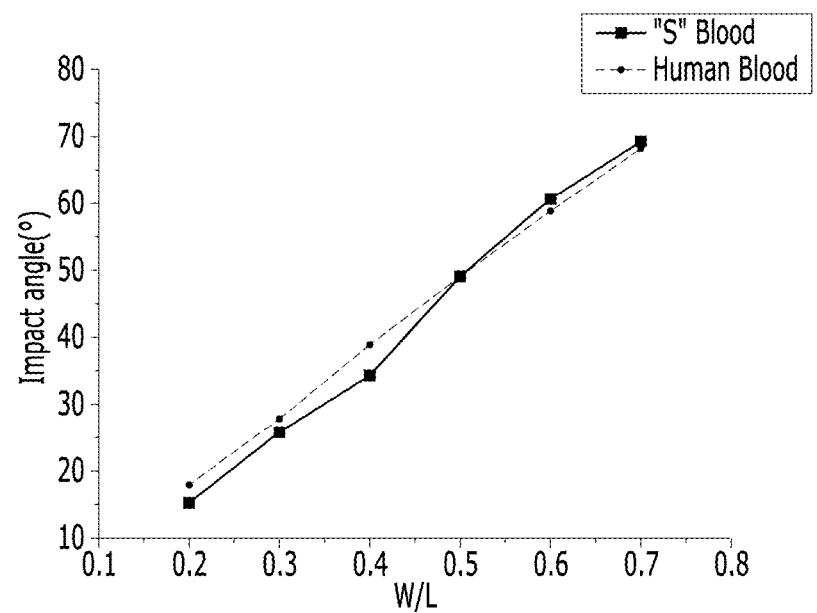
FIG. 9 is a graph showing the comparison of coordinate characteristics of impact angles of falling bloodstains between human blood and Comparative Example 2.
Figure 10:
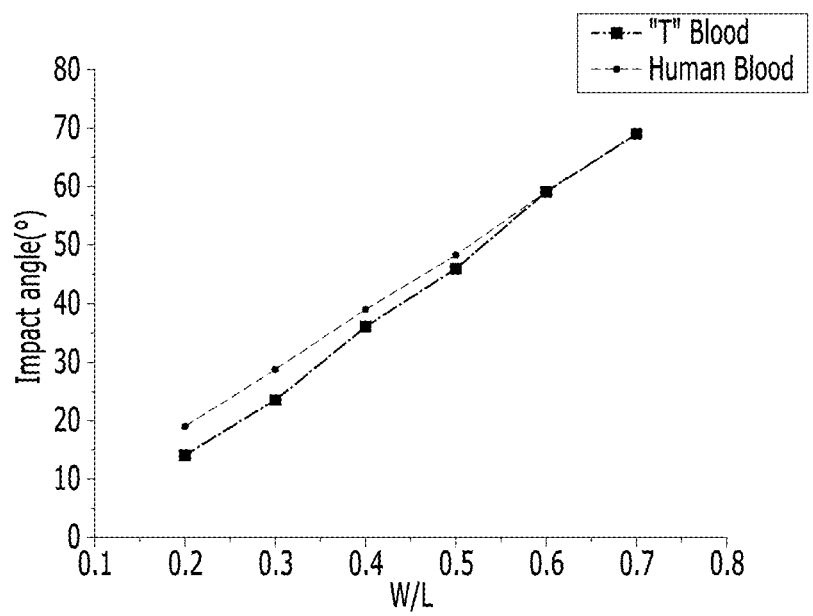
FIG. 10 is a graph showing the comparison of coordinate characteristics of impact angles of falling bloodstains between human blood and Comparative Example 3.
Figure 11:
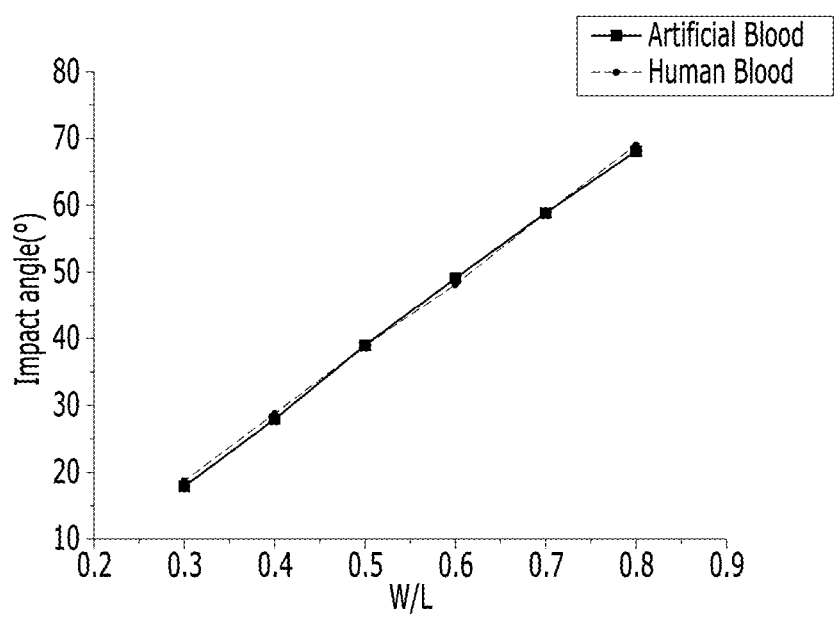
FIG. 11 is a graph showing the comparison of coordinate characteristics of impact angles of falling bloodstains between human blood and Example 1 or 2.

FIG. 8 is a graph showing the comparison of coordinate characteristics of impact angles of falling bloodstains between human blood and Comparative Example 1. FIG. 9 is a graph showing the comparison of coordinate characteristics of impact angles of falling bloodstains between human blood and Comparative Example 2. FIG. 10 is a graph showing the comparison of coordinate characteristics of impact angles of falling bloodstains between human blood and Comparative Example 3. FIG. 11 is a graph showing the comparison of coordinate characteristics of impact angles of falling bloodstains between human blood and Example 1 or 2.

Referring to FIGS. 7 to 11, it can be seen that Example 1 or 2 exhibits coordinate characteristics of impact angles of falling bloodstains closer to that of human blood than Comparative Examples 1 to 3.

Experimental Example 4: Comparison of Coordinate Characteristics of a Spatial Bleeding Site of Bloodstains Scattered by Impact By comparing coordinate characteristics of a spatial bleeding site of bloodstains scattered by impact between human blood, Example 1 or 2, and Comparative Examples 1 to 3, the similarity between Example 1 or 2 and Comparative Examples 1 to 3 and human blood may be confirmed.

Figure 12:
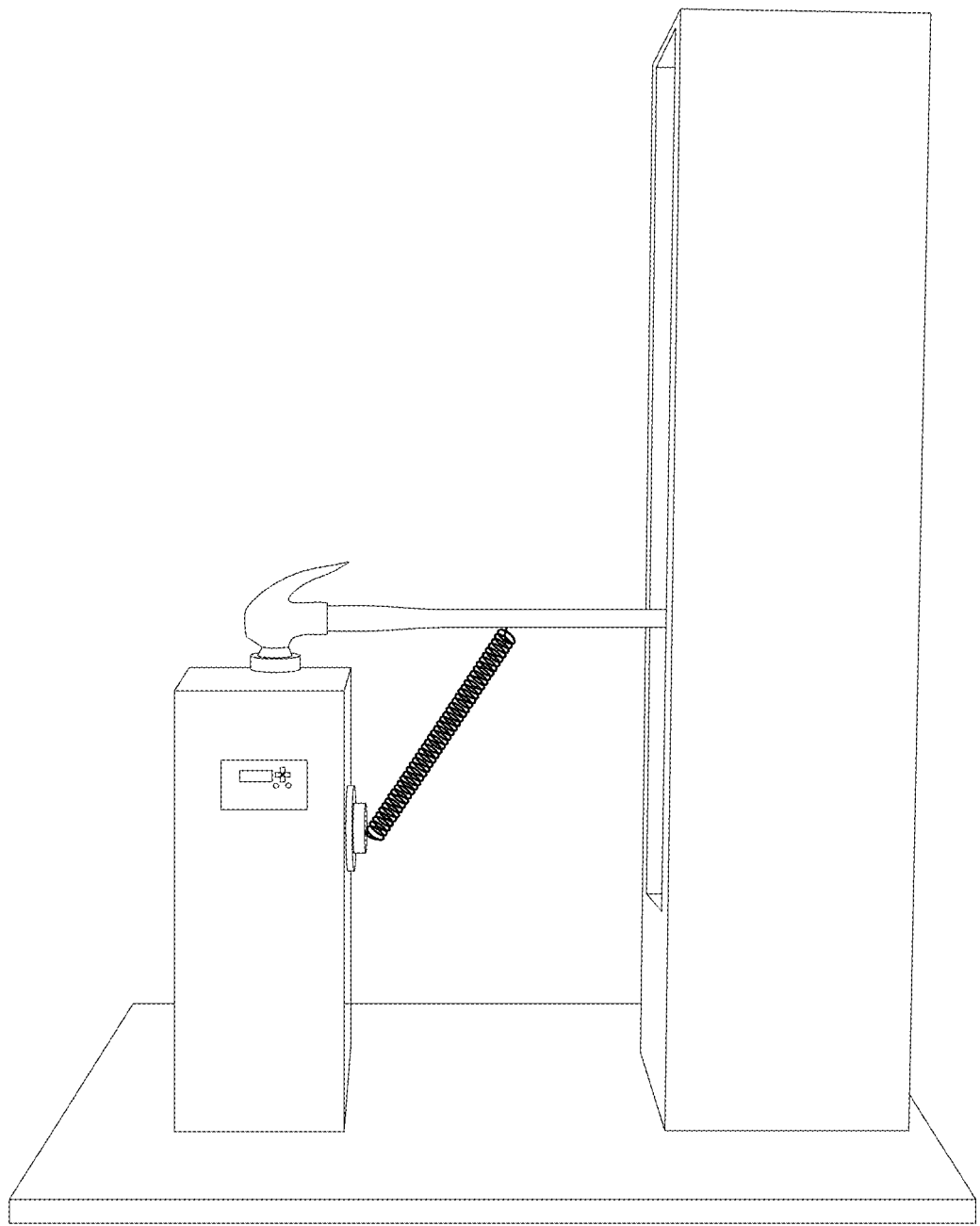
FIG. 12 is a view of a device for generating bloodstains scattered by impact used in an experiment of the disclosure.

FIG. 12 is a view of a device for generating bloodstains scattered by impact used in an experiment of the disclosure. In this comparative experiment, each blood is tested a total of 25 times, 5 times for each blood, under the same conditions of temperature of 37° C., capacity of 2 ml, impact force of 30 kg using the device for generating bloodstains scattered by impact of FIG. 12. Derived experimental values are analyzed using Hemospat (Queen's Univ, Canada) and NST (National Forensic Service, Korea) software.

Each blood is received in a spatial bleeding site (bleeding point) of the device for generating bloodstains scattered by impact of FIG. 12 to generate bloodstains scattered by impact. At this time, the spatial bleeding site may be represented by X, Y, and Z coordinate values in a space. As shown in Table 6, a true value axis for a spatial bleeding site where each blood is accommodated, an estimation origin of area axis derived using measurements after bloodstains scattered by impact are generated, and an estimation origin of area error rate may be displayed.

TABLE 6

| | | True value axis (cm) | | | Estimation origin of area axis (cm) | | | Estimation origin of area error rate (%) | | |
|---|---|---|---|---|---|---|---|---|---|---|
| | Item | X | Y | Z | X | Y | Z | X | Y | Z |
| 1 | Human blood | 30 | 96.7 | 18.6 | 31.6 | 98.5 | 20.4 | 5.3 | 1.9 | 9.7 |
| 2 | Comparative | 30 | 96.7 | 18.6 | 31.9 | 98.8 | 21.5 | 6.3 | 2.1 | 15.5 |

TABLE 6-continued

| Item | True value axis (cm) | | | Estimation origin of area axis (cm) | | | Estimation origin of area error rate (%) | | |
|---|---|---|---|---|---|---|---|---|---|
| | X | Y | Z | X | Y | Z | X | Y | Z |
| Example 1 (Company A) | | | | | | | | | |
| 3 Comparative Example 2 (Company S) | 30 | 96.7 | 18.6 | 30.9 | 98.2 | 21.2 | 3.0 | 1.5 | 13.9 |
| 4 Comparative Example 3 (Company T) | 30 | 96.7 | 18.6 | 31.3 | 99.1 | 22.3 | 4.3 | 2.4 | 19.8 |
| 5 Example 1 or 2 | 30 | 96.7 | 18.6 | 31.1 | 98.2 | 19.7 | 3.6 | 1.5 | 5.9 |

Figure 13:
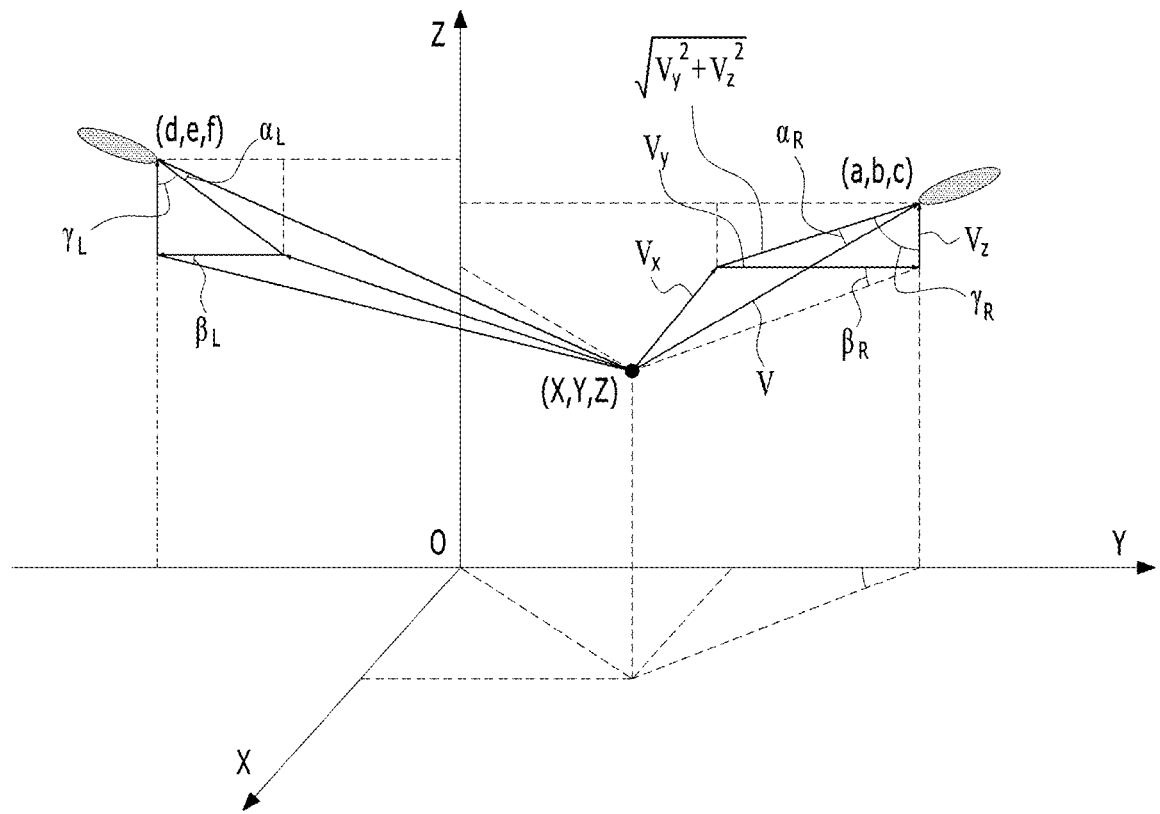
FIG. 13 is a view showing a geometric analysis of coordinates of an estimation origin of area axis of bloodstains scattered by impact in an experimental example of the disclosure.

FIG. 13 is a view showing a geometric analysis of coordinates of a spatial bleeding site of bloodstains scattered by impact in an experimental example of the disclosure. Referring to FIG. 13, using a coordinate, an impact angle (a), and a direction angle (y) of bloodstains scattered by impact at two points as measurements, an estimation origin of area axis is given as follows by a geometric analysis:

$$X = \frac{D \sin \beta_L \sin \beta_R}{\sin(\beta_L + \beta_R)}$$

$$Y = \frac{D \cos \beta_L \sin \beta_K}{\sin(\beta_L + \beta_R)}$$

$$Z = c - \frac{X}{\tan \beta \tan \gamma}.$$

Wherein $$\beta_L = \arctan\left[\frac{\tan \alpha_L}{\tan \gamma_L}\right]$$

$$\beta_R = \arctan\left[\frac{\tan \alpha_R}{\tan \gamma_R}\right],$$

and D is a distance between the bloodstains scattered by impact at two points.

Figure 14:
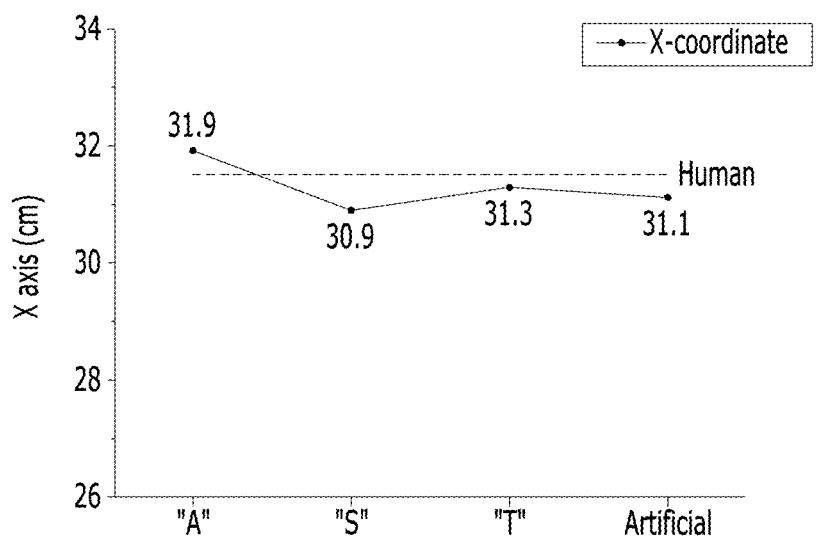
FIG. 14 is a view showing the comparison of X-coordinate characteristics of estimation origin of area axes of human blood, Example 1 or 2, and Comparative Examples 1 to 3.
Figure 15:
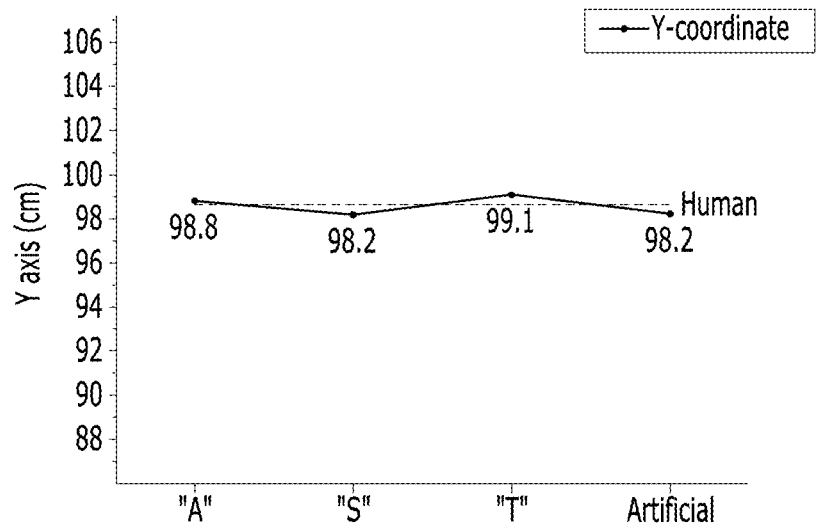
FIG. 15 is a graph showing the comparison of Y-coordinate characteristics of estimation origin of area axes of human blood, Example 1 or 2, and Comparative Examples 1 to 3.
Figure 16:
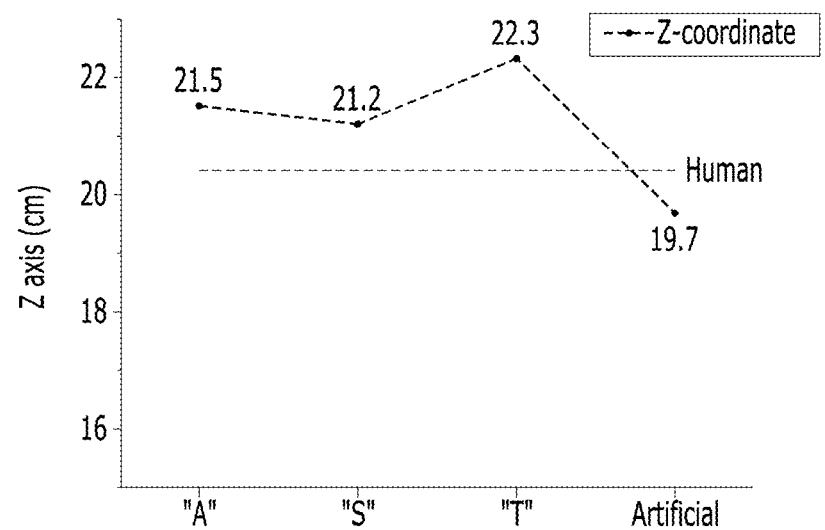
FIG. 16 is a graph showing the comparison of Z-coordinate characteristics of estimation origin of area axes of human blood, Example 1 or 2, and Comparative Examples 1 to 3.

FIG. 14 is a graph showing the comparison of X-coordinate characteristics of estimation origin of area axes of human blood, Example 1 or 2, and Comparative Examples 1 to 3, and FIG. 15 is a graph showing the comparison of Y-coordinate characteristics of estimation origin of area axes of human blood, Example 1 or 2, and Comparative Examples 1 to 3. FIG. 16 is a graph showing the comparison of Z-coordinate characteristics of estimation origin of area axes of human blood, Example 1 or 2, and Comparative Examples 1 to 3.

Referring to Table 6 and FIGS. 14 to 16, X, Y, and Z coordinate values of the estimation origin of area axes of Example 1 or 2 and Comparative Examples 1 to 3 are not significantly different from X, Y, and Z coordinate values of the estimation origin of area axes of human blood.

Experimental Example 5: Comparison of Luminol Reaction Forces

The similarity between Example 1 or 2 and Comparative Examples 4 to 6 and human blood may be confirmed by comparing luminol reaction force of human blood with luminol reaction forces of Example 1 or 2 and Comparative Examples 4 to 6. When a luminol reagent is applied to human blood, a luminol reaction that emits blue-white fluorescent light occurs.

In this experiment comparison, the amount of each blood and the amount of Bluestar (SIRCHIE, USA), a reagent based on luminol, are applied under the same conditions as 20 μl, and the reaction forces are compared through photography.

Figure 17:
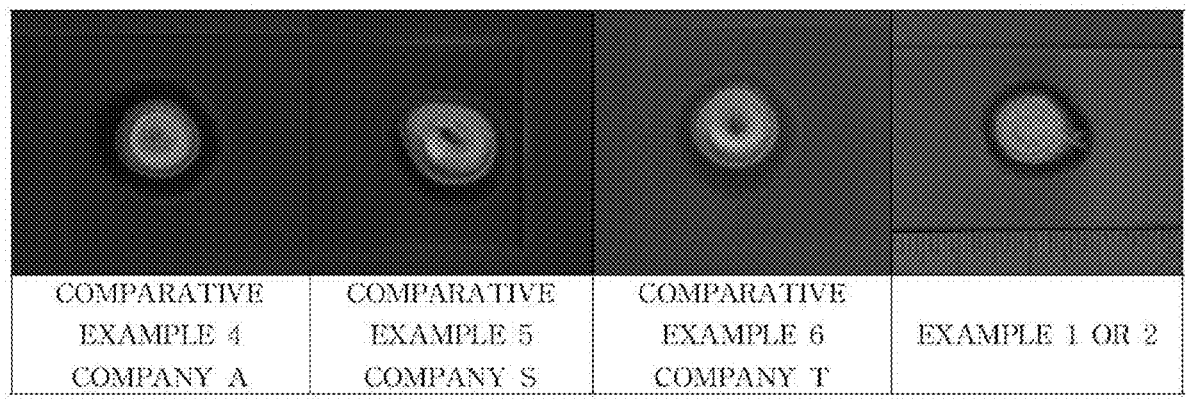
FIG. 17 is a view comparing luminol reaction forces of human blood, Example 1 or 2, and Comparative Examples 4 to 6.

FIG. 17 is a view comparing luminol reaction forces of human blood, Example 1 or 2, and Comparative Examples 4 to 6. Referring to FIG. 17, it can be seen that in Example 1 or 2 and Comparative Examples 4 to 6, similar luminescence of blue-white color through a luminol reaction occurs in a comparative experiment of luminol reaction forces.

Experimental Example 6: Comparison of Staining Power of Bloodstains with Metamorphosis Reagents that react to proteins in bloodstains are used when enhancement through staining of bloodstains with metamorphosis (bloody fingerprints, bloody footprints, etc.) is required. Therefore, for an experiment of bloodstains with metamorphosis, there are various problems such as discomfort because only human blood or animal blood can be used.

Figure 18:
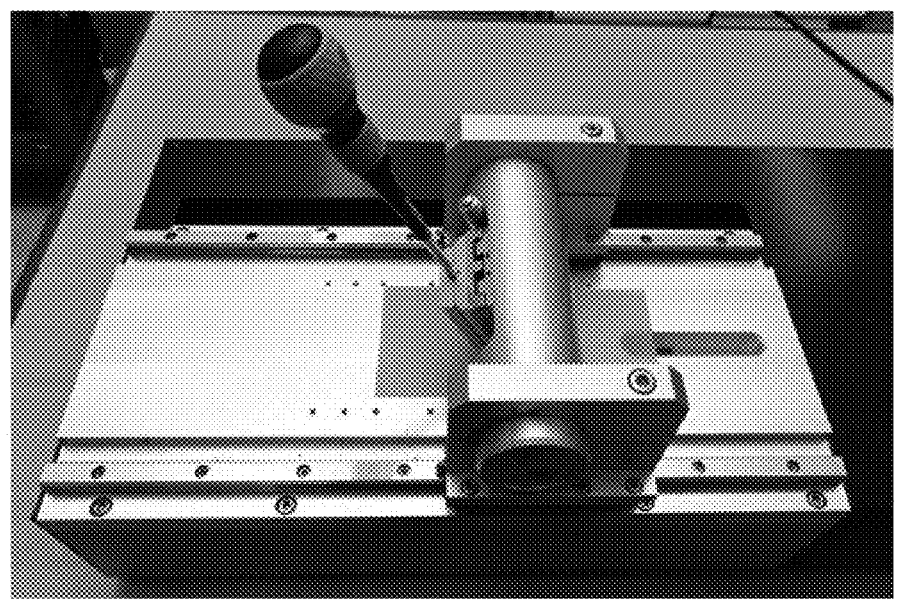
FIG. 18 is a view of a tool mark generator used in an experiment of the disclosure.
Figure 19:
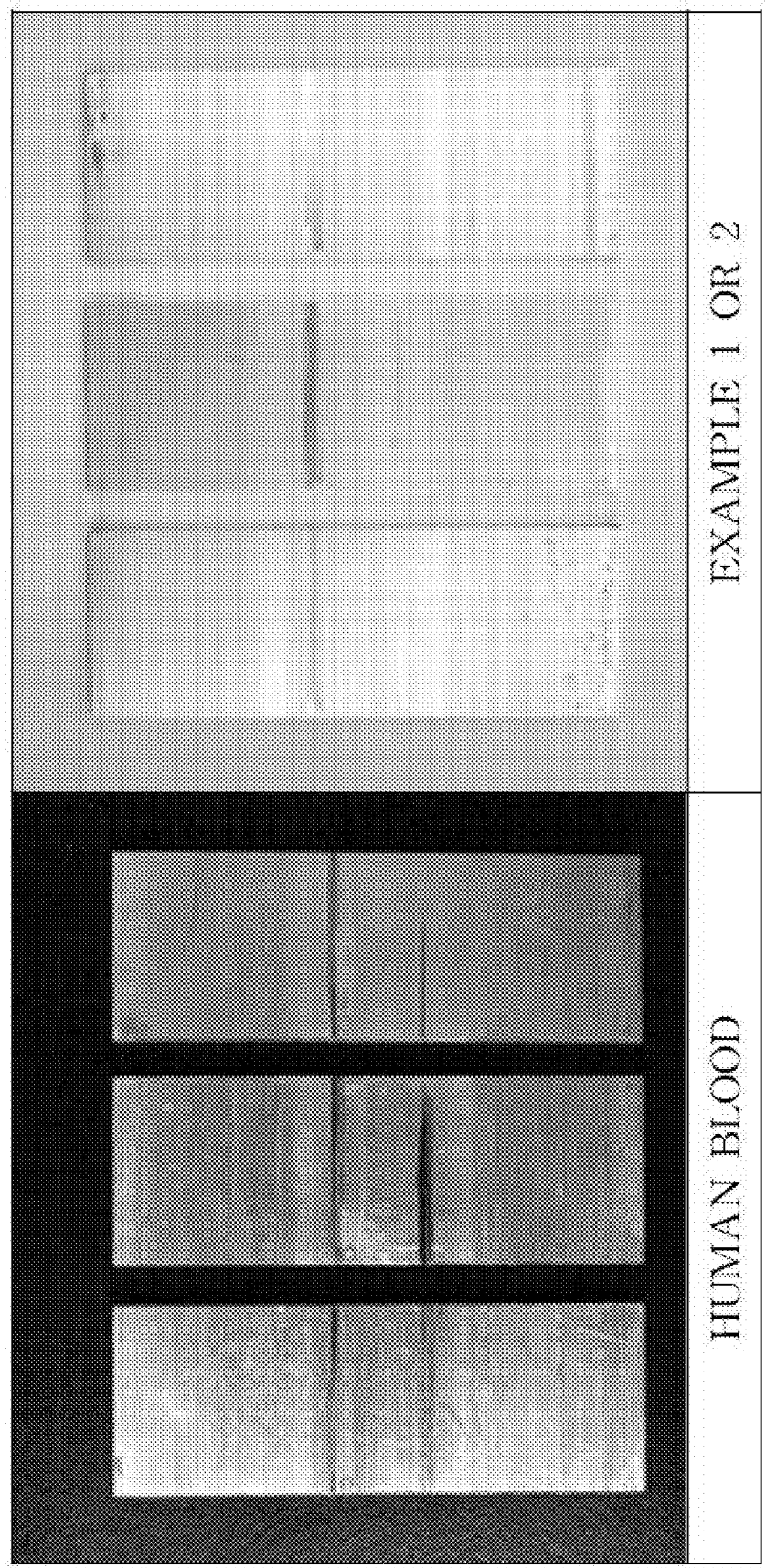
FIG. 19 is a view showing a state in which bloodstains with metamorphosis (wiped bloodstains) are respectively generated on an iron plate (non-porous surface) using human blood and Example 1 or 2.
Figure 20:
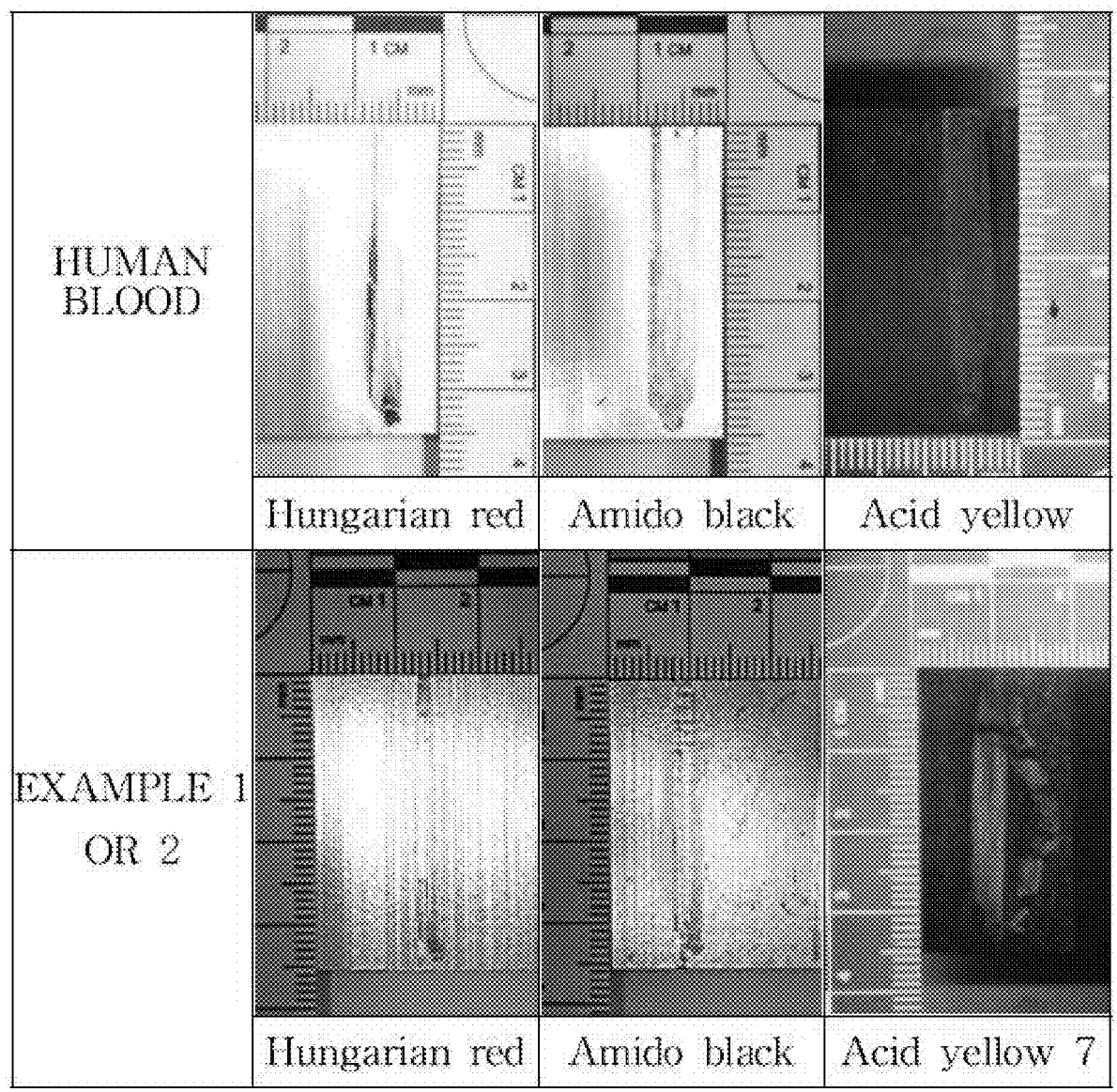
FIG. 20 is a view comparing staining powers of bloodstains with metamorphosis (wiped bloodstains) of human blood and Example 1 or 2.

FIG. 18 is a view of a tool mark generator used in an experiment of the disclosure. FIG. 19 is a view showing a state in which bloodstains with metamorphosis (wiped bloodstains) are respectively generated on an iron plate (non-porous surface) using human blood and Example 1 or 2. FIG. 20 is a view comparing staining powers of bloodstains with metamorphosis (wiped bloodstains) of human blood and Example 1 or 2.

In this experiment comparison, after the amount of human blood and the amount of Example 1 or 2 are set to 0.5 μl respectively and dropped on a non-porous iron plate, bloodstains with metamorphosis (wiped bloodstains) are generated as shown in FIG. 19 with constant force using the tool mark generator of FIG. 18. After staining the resulting bloodstains with metamorphosis (wiped bloodstains) with Hungarian red, Amido black, and Acid yellow7 (SIRCHIE products, USA), which are protein staining reagents, the staining powers are compared.

Referring to FIG. 20, it can be seen that Example 1 or 2 is enhanced by staining in response to Hungarian red, Amido black, Acid yellow7, which are protein staining reagents, in the same manner as human blood.

According to embodiments, artificial blood for a bloodstain pattern analysis may take into account various properties such as viscosity, surface tension, and viscoelasticity and may implement physical properties closer to those of human blood to provide education and experiments on the bloodstain pattern analysis.

In addition, according to embodiments, the artificial blood for the bloodstain pattern analysis may be stored for a long time by excluding the use of material components harmful to the human body as much as possible and by selecting and mixing preservatives that do not interfere with the realization of physical properties.

In addition, according to embodiments, the artificial blood for the bloodstain pattern analysis may not only implement physical properties closer to those of human blood, but also add functionalities such as luminol reaction force and staining power of bloodstain with metamorphosis (bloody fingerprints, bloody footprints, etc.) to increase the efficiency of use.

In addition, according to embodiments, by the artificial blood for the bloodstain pattern analysis that is more similar to human blood, instead of human blood, animal blood, and the existing artificial blood, it is possible to reconstruct the scene of a bloody event and contribute to the analysis and resolution of a crime event.

The embodiments disclosed in the present specification and drawings are merely presented as specific examples to aid understanding, and are not intended to limit the scope of the disclosure. It is obvious to one of ordinary skill in the art to which the disclosure pertains that other modifications based on the technical idea of the disclosure can be implemented in addition

What is claimed is:

1. Artificial blood for a bloodstain pattern analysis comprising:
    water, an amino acid solution, bovine serum albumin, hemoglobin from bovine blood, potassium ferricyanide, sodium hyaluronate, sodium chloride, and tar color.

2. The artificial blood for the bloodstain pattern analysis of claim 1, wherein the amino acid solution comprises L-serine, glycine, DL-alanine, L-lysine, L-leucine, L-threonine, L-asparagin anhydrous, L-histidine, L-valine, sodium chloride, magnesium chloride hexahydrate, calcium chloride anhydrous, and zinc chloride.

3. The artificial blood for the bloodstain pattern analysis of claim 2, comprising:
    4.5% to 5.5% by weight of L-serine, 2.5% to 3.5% by weight of glycine, 1.0% to 2.0% by weight of DL-alanine, 1.5% to 2.5% by weight of L-lysine, 0.1% to 1.0% by weight of L-leucine, 0.5% to 1.0% by weight of L-threonine, 0.5% to 1.0% by weight of L-anhydrous asparagine, 0.5% to 1.0% by weight of L-histidine, 0.1% to 0.8% by weight of L-valine, 30% to 40% by weight of sodium chloride, 0.0001% to 0.0005% by weight of magnesium chloride hexahydrate, 0.0001% to 0.0015% by weight of calcium chloride anhydrous, and 0.0001% to 0.0005% by weight of zinc chloride with respect to 100% by weight of the artificial blood for the bloodstain pattern analysis.

4. The artificial blood for the bloodstain pattern analysis of claim 1, comprising:
    25% to 30% by weight of water, 40% to 50% by weight of amino acid solution, 0.5% to 2% by weight of bovine serum albumin, 0.01% to 0.2% by weight of hemoglobin from bovine blood, 1.5% to 3% by weight of potassium ferricyanide, 20% to 25% by weight of sodium hyaluronate, 0.5% to 1.5% by weight of sodium chloride, and 0.6% to 2% by weight of tar color with respect to 100% by weight of the artificial blood for the bloodstain pattern analysis.

5. The artificial blood for the bloodstain pattern analysis of claim 1, further comprising:
    phenoxyethanol acting as a preservative.

6. The artificial blood for the bloodstain pattern analysis of claim 5, comprising:
    0.1% to 0.7% by weight of phenoxyethanol with respect to 100% by weight of artificial blood for a blood pattern analysis.

7. The artificial blood for the bloodstain pattern analysis of claim 1, wherein the tar color comprises food tar color Red No. 504 (R #504) and food tar color Violet No. 401 (V #401).

* * * * *